United States Patent
Lasota

(10) Patent No.: US 6,916,468 B2
(45) Date of Patent: Jul. 12, 2005

(54) POST-FOAMING SHAVE GEL

(75) Inventor: Andrew Lasota, London (GB)

(73) Assignee: The Gillette Company, Boston, MA (US)

( * ) Notice: Subject to any disclaimer, the term of this patent is extended or adjusted under 35 U.S.C. 154(b) by 7 days.

(21) Appl. No.: 10/442,672

(22) Filed: May 21, 2003

(65) Prior Publication Data
US 2004/0018167 A1 Jan. 29, 2004

Related U.S. Application Data

(63) Continuation of application No. PCT/US01/48730, filed on Dec. 13, 2001, now abandoned.

(30) Foreign Application Priority Data

Dec. 14, 2000 (GB) .............................................. 0030503

(51) Int. Cl.$^7$ ................................................. A61K 7/15
(52) U.S. Cl. ................... 424/73; 424/70.11; 424/70.13; 424/70.17; 424/70.19; 424/70.27; 424/70.31
(58) Field of Search ............................... 424/73, 70.11, 424/70.13, 70.17, 70.19, 70.27, 70.31, 703.1; 514/772, 772.4, 772.7, 781, 788, 788.1, 944, 945, 975

(56) References Cited

U.S. PATENT DOCUMENTS

| | | | |
|---|---|---|---|
| 2,995,521 A | 8/1961 | Estignard-Bluard | 252/90 |
| 3,541,581 A | 11/1970 | Monson | 252/90 |
| 4,046,874 A | 9/1977 | Gabby et al. | 424/73 |
| 4,405,489 A | 9/1983 | Sisbarro | 252/315.4 |
| 4,528,111 A | 7/1985 | Su | 252/107 |
| 4,651,503 A | 3/1987 | Anderson, III et al. | 53/440 |
| 4,761,279 A | 8/1988 | Khalil et al. | 424/73 |
| 4,892,729 A | 1/1990 | Cavazza | 424/73 |
| 4,999,183 A | 3/1991 | Mackles et al. | 424/47 |
| 5,248,495 A | 9/1993 | Patterson et al. | 424/73 |
| 5,308,643 A | 5/1994 | Osipow et al. | 424/73 |
| 5,326,556 A | 7/1994 | Barnet et al. | 424/73 |
| 5,500,211 A | 3/1996 | George et al. | 424/73 |
| 5,902,574 A | 5/1999 | Stoner et al. | 424/73 |

FOREIGN PATENT DOCUMENTS

| | | |
|---|---|---|
| WO | 91/07943 | 6/1991 |
| WO | 92/16188 | 10/1992 |

OTHER PUBLICATIONS

STN/CAS online, file PROMT, Acc. No. 90:45191 (International Product Alert (Jan. 17, 1990)),Abstract.*

* cited by examiner

Primary Examiner—S. Mark Clardy
Assistant Examiner—Frank Choi
(74) Attorney, Agent, or Firm—Stephan P. Williams

(57) ABSTRACT

A soap-free self-foaming shave gel composition is disclosed which maintains superior performance attributes while avoiding the harshness and drying associated with soap-based and other ionic shave preparations. The composition is a non-ionic shave gel composition which comprises water, a water-insoluble fatty alcohol, a non-ionic emulsifier, a volatile self-foaming agent, and a non-volatile paraffinic hydrocarbon fluid.

20 Claims, No Drawings

POST-FOAMING SHAVE GEL

This application is a continuation of International Application PCT/US01/48730 filed Dec. 13, 2001, now abandoned.

This invention relates to a post-foaming shave gel composition. Such a composition is dispensed in the form of a gel containing a volatile component that causes the gel to turn into a foam when spread on the skin in preparation for wet shaving, that is shaving with a razor blade.

Post-foaming or self-foaming shave gels are well-known and have been described, for example, in U.S. Pat. Nos. 2,995,521 (Bluard), 3,541,581 (Monson), 4,405,489 (Sisbarro), 4,528,111 (Su), 4,651,503 (Anderson), 5,248,495 (Patterson), 5,308,643 (Osipow), 5,326,556 (Barnet) and PCT WO 91/07943 (Chaudhuri). Such compositions generally take the form of an oil-in-water emulsion in which the self-foaming agent, generally a volatile (i.e. low boiling point) aliphatic hydrocarbon is solubilized in the oil phase, and the water phase comprises a water-soluble soap component. The product is generally packaged in an aerosol container with a barrier, such as a piston or collapsible bag, to separate the self-foaming gel from the propellant required for expulsion of the product. The product is dispensed as a clear, translucent or opaque gel that is substantially free from foaming until it is spread over the skin, at which time it produces a foam lather generated by the volatilization of the volatile hydrocarbon foaming agent.

While the conventional self-foaming shave gels have gained wide acceptance by consumers, they can be somewhat harsh and drying to the skin due to the soap component. To counteract this effect, the typical shave gel composition is formulated with skin soothing components such as humectants, emollients, silicones, etc. While the addition of such components substantially improves the aesthetics of the product, repeated use can still produce undesirable drying of the skin, particularly among female users.

With a view to reducing or avoiding this problem, certain soap-free shaving products have been developed. Thus, U.S. Pat. No. 5,500,211 (George) describes post-foaming shave gel compositions which are free of soap but instead contain certain N-acyl sarcosinate salts which are anionic surfactants.

U.S. Pat. No. 4,892,729 (Cavazza) describes a soap-free non-aerosol, non-lathering shave cream and U.S. Pat. Nos. 4,046,874 (Gabby) and 4,761,279 (Khalli) disclose soap-free shaving cream compositions containing, respectively, a polyglycerol fatty ester (e.g. triglycerol monostearate) and a salt of a fatty ester of lactylic acid (e.g. sodium salt of stearyl lactylic acid). Also, a pre-shave gel containing polyethylene oxide polymer and polysulfonic acid polymer is disclosed in U.S. Pat. No. 4,999,183 (Mackles).

Whilst the use of soap-free formulations does reduce problems associated with soap-based products, we have recognized that the presence of ionic species in the formulations still gives rise to various undesirable effects such as swelling. This is because skin protein is amphoteric and can thus interact with ionic species. There is, therefore, a need for a non-ionic post-foaming shave gel composition whereby problems arising from the use of ionic compositions can be avoided. Prior art post-foaming shave gels are all ionic and because the achievement of good post-foaming gel compositions is far from easy, requiring the balancing of a number of factors, there has been a prejudice in the art against moving away from the well-tried ionic (principally soap-based) compositions.

We have now found, however, that it is in fact possible to make satisfactory non-ionic post-foaming shave gels, and thereby to avoid subjecting the skin to the effects of ionic conditions. This is particularly advantageous both in respect of sensitive skins and also more generally having regard to the fact that in the shaving process, the skin is abraded and likely to be damaged. We have further found that certain preferred compositions show other advantages over the soap-based prior known compositions in addition to the advantage of being non-ionic.

The present invention comprises a soap-free self-foaming shave gel composition which maintains superior performance attributes while avoiding the harshness and drying associated with soap-based and other ionic shave preparations. The non-ionic shave gel composition of the present invention comprises water, a water-insoluble fatty alcohol, a non-ionic emulsifier, a volatile self-foaming agent, and a non-volatile paraffinic hydrocarbon fluid.

The essential components of the shaving composition of the present invention include, in percent by weight, about 60 to 90% water; about 2 to 20% of at least one $C_{12}$–$C_{18}$ water-insoluble normally solid fatty alcohol, an emulsifier comprising from 0.2 to 10% of a $C_{14}$–$C_{22}$ fatty alcohol ethoxylated with from 50 to 150 mole ethylene oxide (higher ethoxylated fatty alcohol) and from 0 to 20% of a $C_{12}$–$C_{18}$ fatty alcohol ethoxylated with from 15 to 30 mole ethylene oxide (lower ethoxylated fatty alcohol); about 0.5 to 10% self-foaming agent, and about 0.5 to 10% non-volatile paraffinic hydrocarbon fluid, said composition being in the form of a self-foaming gel and being substantially free of ions. Preferably the composition will comprise about 70 to 80% water, about 3 to 10% water-insoluble fatty alcohol, from 8 to 12% of the emulsifier comprising about 2.0 to 8% (by weight of the composition) of the highly ethoxylated fatty alcohol, from 2 to % 8% (by weight of the composition) of the lower ethoxylated fatty alcohol, about 1 to 8% self-foaming agent, and about 2 to 10% non-volatile paraffinic hydrocarbon fluid.

By "substantially free of ions" or "non-ionic" we mean that there is no more than 1% by weight of any ionic material in the compositions. Thus, the compositions are substantially free of soaps (including interrupted soaps such as sarcosines) and of anionic surfactants. The compositions of the invention can be totally free of ions and this is preferred unless, as is described more fully hereafter, a small amount (up to 1% by weight) of cationic material is purposely included to have a beneficial effect on the product.

The fatty alcohol(s) per se (i.e. non-ethoxylated fatty alcohol) in the compositions of the invention contains from 12 to 18 carbon atoms and is a water-insoluble normally solid (i.e. at room temperature and atmospheric pressure) saturated or unsaturated alcohol. The liquid unsaturated $C_{18}$ alcohols, such as oleyl alcohol, are not used but the $C_{18}$ saturated alcohols can be used. The $C_{12}$ fatty alcohols are not generally preferred because of their tendency to hydrophilicity. The preferred fatty alcohols are $C_{14}$–$C_{16}$, most preferably myristyl alcohol. The compositions can contain two or more of the fatty alcohols. One preferred mixture is a blend of cetyl and myristyl alcohols. The ratio is not critical.

The amount of water-insoluble fatty alcohol(s) is (in total) from 2 to 20%, preferably from 3 to 10% and most preferably from 5 to 8%, by weight of the shave gel composition.

The compositions of the invention contain an emulsifier to solubilize the solid water-insoluble fatty alcohol component. The emulsifier comprises a water-soluble highly ethoxylated $C_{14}$–$C_{22}$ saturated or unsaturated fatty alcohol. By "highly ethoxylated" we mean having from 50 to 150, preferably from 75 to 125, and most preferably about 100, mole ethylene oxide per mole of fatty alcohol. The chain length of the fatty alcohol can be anywhere in the range $C_{14}$ to $C_{22}$, but we prefer to use $C_{14}$ myristyl, $C_{16}$ cetyl or $C_{18}$ stearyl or oleyl alcohol, i.e. we prefer the emulsifier to comprise highly ethoxylated myristyl, cetyl, stearyl or oleyl alcohol, e.g. myreth-100, ceteth-100, steareth-100 or oleth-100. Two or more of the highly ethoxylated fatty alcohols can be used, as desired.

In addition to the highly ethoxylated $C_{14}$–$C_{22}$ fatty alcohol, the emulsifier preferably also comprises one or more water-soluble lower ethoxylated $C_{12}$–$C_{18}$ saturated or unsaturated fatty alcohols. By "lower ethoxylated" we mean having from 15 to 30, preferably 17 to 25, and most preferably about 20, mole ethylene oxide per mole of fatty alcohol. The chain length of the fatty alcohol can be anywhere in the range $C_{12}$–$C_{18}$. Preferred lower ethoxylated fatty alcohols include oleyl, cetyl, stearyl and myristyl alcohols, e.g. polyoxyethylene-(20)-oleyl alcohol, polyoxyethylene-(20)-cetyl alcohol (ceteth-20), polyoxethylene-(20)-stearyl alcohol, and polyoxyethylene-(20)-myristyl alcohol (myreth-20).

The amount of higher ethoxylated fatty alcohols in the compositions of the invention is from 0.2 to 10% by weight, the preferred amount being from 2 to 8%. When present, the amount of lower ethoxylated fatty alcohols is up to 20%, preferably from 2 to 8%. Preferably, the total amount of higher and lower ethyoxylated fatty alcohols, i.e. of emulsifier, is from 8 to 12%. It is highly preferred that the weight ratio of emulsifier to (free) fatty alcohol be approximately in the range 2:1 to 1:2.

Preferred mixtures for use as emulsifiers include a mixture of steareth (100) and oleth-(20), and a mixture of oleth-(100) and ceteth-(20), for example.

The self-foaming agent may be any suitable volatile material such as a hydrocarbon or an ether, for example, with a sufficiently low boiling point that it will volatilize and foam the gel upon application to the skin, but not so low that it causes the gel to foam prematurely. The typical boiling point of such an agent generally falls within the range of 20° to 40° C. The self-foaming agent will normally be present in an amount comprising about 0.5 to 10% of the composition, preferably about 1 to 8%, by weight. Preferred self-foaming agents are selected from saturated aliphatic hydrocarbons having 4 to 6 carbon atoms, such as n-pentane, isopentane, neopentane, n-butane, isobutane, and mixtures thereof. Most preferred is pure isobutane at about 2 to 4% by weight or a mixture of isobutane and isopentane (3:1).

The shaving composition additionally contains about 1 to 10%, preferably about 2 to 10%, most preferably from 4 to 8%, of a non-volatile paraffinic hydrocarbon fluid which aids in gelling the composition. The terms "non-volatile" and "fluid" mean that these materials are liquid at room temperature and have a boiling point above 200° C. Such hydrocarbon fluids include mineral oils and branched-chain aliphatic liquids. These fluids typically have from about 16 to about 48, preferably about 20 to about 40, carbon atoms and a viscosity of about 5 to about 100 cs., preferably about 10 to about 50 cs., at 40° C. The preferred non-volatile paraffinic hydrocarbon fluid is selected from mineral oil with a viscosity of about 10 to about 50 cs., at 40° C., hydrogenated polyisobutene with a molecular weight of about 320 to about 420, and mixtures thereof.

Water is the major component of the composition and is used in sufficient quantities to solubilize the surfactant component and form the continuous phase of the emulsion, while providing a stable gel of suitable viscosity with desirable lathering and rinsing properties. It is added in a sufficient amount (q.s.) to bring the total of all components to 100%. The quantity of water in the composition typically falls within the range of about 60 to 90%, preferably about 65 to 85%, most preferably about 70 to 80%.

In addition, to the above-described essential components, the shaving composition of the present invention may include a variety of other well-known cosmetic ingredients to improve the aesthetics and performance characteristics of the composition, provided that all such ingredients are non-ionic except as hereinafter described.

For example, it may be desirable to include a water-soluble rheology modifier which reduces the viscosity but increases the "body" of the gel. The most preferred such modifier is polyethylene oxide or polyacrylamide (MW 5 to 6 million). For example, for polyethylene oxide of molecular weight 5 m, am amount of about 0.01 to 0.5% is satisfactory, and for polyacrylamide, an amount of 0.01 to 0.5% is satisfactory. Examples of other modifiers include, for example, non-ionic hydroxyalkyl cellulose polymers such as hydroxyethyl cellulose and hydroxypropyl cellulose (sold under the trademarks "Natrosol" and "Klucel" respectively), carboxymethyl cellulose, and cellulose methyl ether (sold under the trademark "Methocel"). Resins and starches may also be used. Of these other modifiers, hydroxyethyl cellulose, hydroxypropyl cellulose, and mixtures thereof are preferred and are typically included in an amount of about 0.01 to 5%, preferably about 0.1 to 1%, by weight of the composition.

There are a number of ionic substances which are known to have useful properties when included in topical compositions. However, in many prior known ionic shaving compositions, the presence of these cationic materials is not very effective because the gels usually also contain other ionic substances such as surfactants which can mask the beneficial effects sought or have a contrary non-beneficial effect themselves.

We have now found, however, that a small amount (up to about 1% by weight) of an ionic material such as a cationic conditioning agent, can be included in the otherwise non-ionic compositions of the present invention to advantage. That is to say, because the gels of the invention are essentially non-ionic, a small amount of a beneficial ionic material can exert a noticeable effect. The invention thus includes compositions which contain up to about 1% of an ionic material. Suitable ionic materials are cationic skin conditioning agents to provide in-shave lubrication and post-shave skin feel. These materials are well known in the art and are commercially available. Examples include polymers containing quaternary nitrogen groups such as Polyquaternium −4, −10, −11, −16, −28, −29, −30, −32, −33, −37 and −47, which could suitably be used in amounts of from 0.1 to 1.0% by weight of the compositions.

In a further aspect of the present invention, there is provided a completely ion-free self-foaming shaving gel in which has been included up to 1% by weight of the gel, of an ionic material.

Other additives which may be utilized in the compositions of the invention include humectants such as glycerin, sorbitol, and propylene glycol, skin freshening and soothing agents such as menthol, aloe, allantoin and collagen, lubricants such as polyethylene oxide, and silicones (e.g. dimethicone, dimethiconol, dimethicone copolyol, stearyl dimethicone, cetyl dimethicone copolyol, phenyl dimethicone, cyclomethicone, etc.), vitamins (including vitamin precursors and derivatives), colorants, fragrances, antioxidants and preservatives. The use of polyethylene oxide and/or polyacrylamide as a lubricant is a secondary role (see above for use as a rheology modifier). As a lubricant, it is used in greater amounts, e.g. up to about 1%.

The shaving composition of the present invention is for dispensing from an aerosol container with a barrier, such as a collapsible bag or piston, to separate the gel from the propellant required for expulsion.

The non-ionic post-foaming shave gels of the invention are clear gels. The blend of water-insoluble fatty alcohol(s) per se and water-soluble fatty alcohol ethoxylate(s) creates a balance of hydrophilic/lipophilic moieties which mimics the physical chemistry properties of soap and is partially water soluble and so able to form a stable bubble structure. Thus, the gels of the invention can provide the properties of a conventional soap-based post-foaming gel but without the disadvantage of being ionic.

In order that the invention may be more fully understood, the following Examples are given by way of illustration only.

EXAMPLE 1

A non-ionic post-foaming shaving gel was made of the following composition:

|                   | % w/w  |
|-------------------|--------|
| Deionised Water   | 73.4   |
| Myreth-20         | 7.8    |
| Myristyl alcohol  | 7.0    |
| Mineral Oil       | 5.0    |
| Myreth-100        | 3.0    |
| Isobutane         | 2.75   |
| Fragrance         | 1.00   |
| Polyox coagulant  | 0.0025 |
| Dye               | 0.001  |
| Kathon CG         | 0.0006 |

In use, the gel was found to have ease of spreading and lathering and it provided a good lather. Good razor glide over the skin was obtained, giving a comfortable shave with the lather lasting throughout the shave and giving a good lubricating effect throughout the shave.

EXAMPLE 2

A gel of the invention was made of the following composition:

|                             | % w/w |
|-----------------------------|-------|
| Deionised Water             | 74.5  |
| Oleth-20                    | 5.7   |
| Myristyl alcohol            | 5.0   |
| Mineral Oil                 | 5.8   |
| Steareth-100                | 5.0   |
| Isobutane                   | 2.5   |
| Fragrance                   | 1.0   |
| Cetyl alcohol               | 0.8   |
| Polyacrylamide (MW 5 to 6 m)| 0.01  |

Satisfactory results were obtained.

EXAMPLE 3

A variant gel was prepared principally for use as a female shave gel. The changes in composition (from Example 1) were to provide a denser, but lower volume, lather and spreading characteristics more suited to large surface area of skin through the addition of lauryl alcohol. The formula was:

|                   | % w/w  |
|-------------------|--------|
| Deionised Water   | 74.7   |
| Ceteth-20         | 7.8    |
| Myristyl alcohol  | 5.5    |
| Mineral Oil       | 5.0    |
| Steareth-100      | 3.0    |
| Isobutane         | 2.75   |
| Fragrance         | 0.7    |
| Lauryl alcohol    | 0.5    |
| Polyox coagulant  | 0.0025 |
| Dye               | 0.001  |
| Kathon CG         | 0.0006 |

Satisfactory results were obtained.

EXAMPLE 4

A gel of the invention was made of the following composition:

|                                         | % w/w |
|-----------------------------------------|-------|
| Myristyl alcohol                        | 6.7   |
| Mineral oil                             | 5.8   |
| Ceteth-20                               | 5.7   |
| Steareth-100                            | 4.6   |
| Isobutane                               | 2.5   |
| Polyacrylamide (5 to 6 M m.wt)          | 0.042 |
| Water, dye, preservative q.s. fragrance | 100   |

Satisfactory results were obtained.

A cationic skin conditioning agent Polyquaternium-10 (Ucare JR-400) was added to the gel in an amount of 0.1% by weight, to form another gel of the invention.

While the invention has been described in detail with particular reference to preferred embodiments thereof, various modifications and substitutions will be apparent to those skilled in the art and should be considered to fall within the spirit and scope of the invention as defined by the following claims.

What is claimed is:

1. A substantially non-ionic shaving composition in the form of a self-foaming gel comprising, in percent by weight, about 60 to 90% water; about 2 to 20% of at least one $C_{12}$–$C_{18}$ water-insoluble normally solid fatty alcohol; an emulsifier comprising from 0.2 to 10% of at least one ethoxylated $C_{14}$–$C_{22}$ fatty alcohol with from 50 to 150 moles ethylene oxide per mole of fatty alcohol and from 0 to 20% of at least one ethoxylated $C_{12}$–$C_{18}$ fatty alcohol with from 15 to 30 moles ethylene oxide per mole of fatty alcohol; about 0.5 to 10% self-foaming agent; and about 0.5 to 10% non-volatile paraffinic hydrocarbon fluid; said composition being substantially free of ionic material.

2. The shaving composition of claim 1, wherein the emulsifier comprises a mixture of at least one ethoxylated $C_{14}$–$C_{22}$ fatty alcohol with from 50 to 150 moles ethylene oxide per mole of fatty alcohol, and at least one ethoxylated $C_{12}$–$C_{18}$ fatty alcohol with from 15 to 30 moles ethylene oxide per mole of fatty alcohol.

3. The shaving composition of claim 2, wherein the at least one normally solid fatty alcohol comprises a $C_{14}$–$C_{16}$ fatty alcohol.

4. The shaving composition of claim 3, wherein the at least one normally solid fatty alcohol comprises myristyl alcohol.

5. The shaving composition of claim 2, wherein the at least one normally solid fatty alcohol comprises a blend of myristyl alcohol and cetyl alcohol.

6. The shaving composition of claim 2, which contains from 3 to 10% by weight of said at least one normally solid fatty alcohol.

7. The shaving composition of claim 2, wherein the at least one ethoxylated $C_{14}$–$C_{22}$ fatty alcohol with from 50 to 150 moles ethylene oxide per mole of fatty alcohol comprises ethoxylated stearyl alcohol, ethoxylated oleyl alcohol, ethoxylated myristyl alcohol or ethoxylated cetyl alcohol, with from 50 to 150 moles ethylene oxide per mole of fatty alcohol.

8. The shaving composition of claim 7, wherein the at least one ethoxylated $C_{12}$–$C_{18}$ fatty alcohol with from 15 to 30 moles ethylene oxide per mole of fatty alcohol comprises ethoxylated cetyl alcohol, ethoxylated oleyl alcohol, ethoxylated stearyl alcohol, or ethoxylated myristyl alcohol with from 15 to 30 moles ethylene oxide per mole of fatty alcohol.

9. The shaving composition of claim 2, wherein the at least one ethoxylated $C_{14}$–$C_{22}$ fatty alcohol with from 50 to 150 moles ethylene oxide per mole of fatty alcohol comprises an ethoxylated $C_{14}$–$C_{22}$ fatty alcohol with from 75 to 125 moles ethylene oxide per mole of fatty alcohol.

10. The shaving composition of claim 9, wherein the at least one ethoxylated $C_{12}$–$C_{18}$ fatty alcohol with from 15 to 30 moles ethylene oxide per mole of fatty alcohol comprises an ethoxylated $C_{12}$–$C_{18}$ fatty alcohol with from 17 to 25 moles ethylene oxide per mole of fatty alcohol.

11. The shaving composition of claim 2, wherein the emulsifier comprises a mixture of steareth-100 and oleth-20, or a mixture of oleth100 and ceteth-20.

12. The shaving composition of claim 1, which contains from 8 to 12% of said emulsifier.

13. The shaving composition of claim 1, wherein the non-volatile paraffinic hydrocarbon fluid has about 20 to about 40 carbon atoms and a viscosity of about 10 to about 50 cs. at 40°C.

14. The shaving composition of claim 13, wherein the non-volatile paraffinic hydrocarbon fluid is selected from the group consisting of mineral oils, branched-chain aliphatic liquids, and mixtures thereof.

15. The shaving composition of claim 1, wherein the self-foaming agent is a volatile saturated aliphatic hydrocarbon having 4 to 6 carbon atoms, or a mixture of two or more such hydrocarbons.

16. The shaving composition of claim 1, which additionally comprises a thickening agent selected from the group consisting of polyethylene oxide, polyacrylamide, hydroxyethyl cellulose, hydroxypropyl cellulose, and mixtures thereof.

17. The shaving composition of claim 1, which comprises, in percent by weight, about 70 to 80% water; about 3 to 10% of one or more $C_{12}$–$C_{18}$ water-insoluble normally solid fatty alcohols; from 8 to 12% of an emulsifier comprising from 2 to 8% (by weight of the composition) of an ethoxylated $C_{12}$–$C_{18}$ fatty alcohol with about 75 to 125 moles of ethylene oxide per mole of fatty alcohol, and from 2 to 8% (by weight of the composition) of an ethoxylated $C_{12}$–$C_{18}$ fatty alcohol with from 17 to 25 moles ethylene oxide per mole of fatty alcohol; about 1 to 8% self-foaming agent; and about 2 to 10% non-volatile paraffinic hydrocarbon fluid.

18. The shaving composition of claim 17, which is substantially free of soaps (including interrupted soaps) and of anionic surfactants.

19. The shaving composition of claim 18, which contains up to 1% by weight of a cationic skin conditioning agent.

20. An aerosol dispenser containing a substantially nonionic shaving composition as claimed in claim 1.

* * * * *